United States Patent [19]
Siepser

[11] Patent Number: 4,734,095
[45] Date of Patent: * Mar. 29, 1988

[54] SELF-CENTERING ARTIFICIAL INTROAOCULAR LENS

[76] Inventor: Steven B. Siepser, 866 Downingtown Pk., West Chester, Pa. 19380

[*] Notice: The portion of the term of this patent subsequent to Dec. 10, 2002 has been disclaimed.

[21] Appl. No.: 11,254

[22] Filed: Feb. 5, 1987

Related U.S. Application Data

[63] Continuation of Ser. No. 770,405, Aug. 25, 1985, abandoned, which is a continuation-in-part of Ser. No. 520,187, Aug. 4, 1983, Pat. No. 4,556,998.

[51] Int. Cl.$^4$ ............................................. A61F 2/16
[52] U.S. Cl. ...................................................... 623/6
[58] Field of Search ............................................ 623/6

[56] References Cited

U.S. PATENT DOCUMENTS 4,556,998 12/1985 Siepser ................................. 623/6

Primary Examiner—Richard J. Apley
Assistant Examiner—James Prizant
Attorney, Agent, or Firm—Eugene E. Renz, Jr.

[57] ABSTRACT

An artificial intraocular lens for surgical implantation to replace a damaged natural lens in an otherwise functional eye of a patient is disclosed as having a dome-shaped central disc portion, haptic loops formed on said central portion, for centering said central portion after implantation, wherein the central portion is composed of a dry, solid hydrophilic material capable of hydration by the natural fluid present in the eye to expand after implantation to provide an optically correct lens, wherein the central portion has a cross-sectional dimension substantially less than that of the natural lens and wherein said haptic loops are configured such that said central portion is centered upon implantation and remains centered during expansion thereof, thus improving the vision of the patient.

19 Claims, 16 Drawing Figures

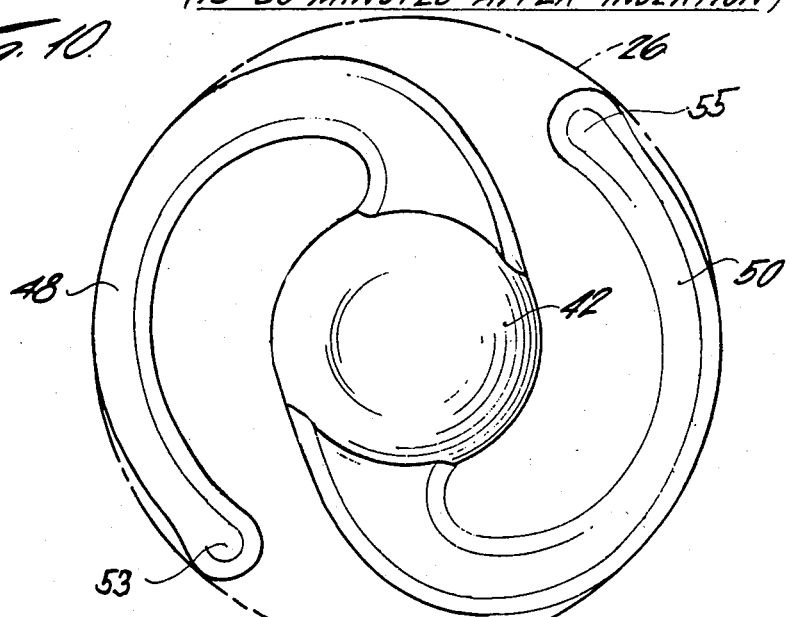
Fig. 10 (15-30 MINUTES AFTER INSERTION)
HAPTICS EXPANDED APRX. 90-170%
LENS PORTION EXPANDED APRX. 30-60%
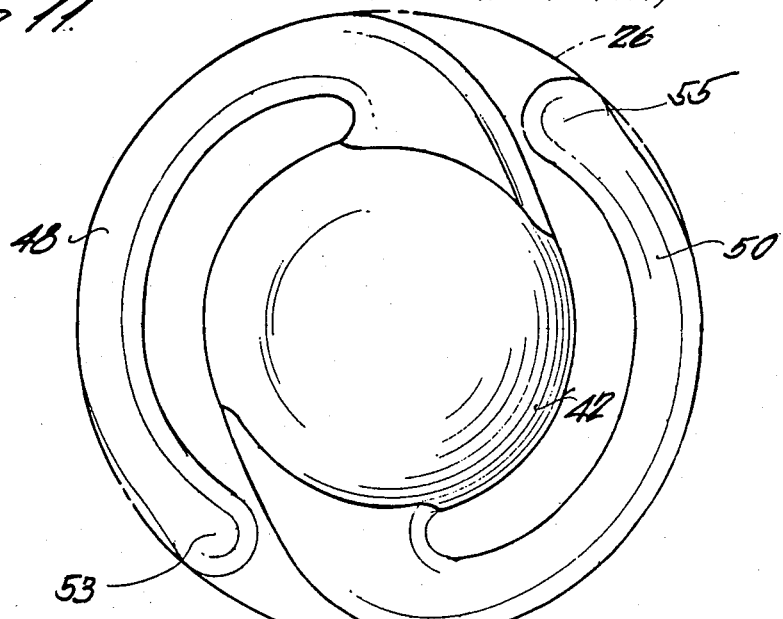
Fig. 11 (90 MINUTES AFTER INSERTION)
IOL FULLY EXPANDED APRX 180%

SELF-CENTERING ARTIFICIAL INTROAOCULAR LENS

This application is a continuation of application Ser. No. 770,405 filed Aug. 25, 1984 (now abandond) which is a continuation-in-part of application Ser. No. 520,187, filed Aug. 4, 1983 entitled IMPROVED ARTIFICIAL INTRAOCULAR LENSES AND METHOD FOR THEIR SURGICAL IMPLANTATION, now U.S. Pat. No. 4,556,998.

BACKGROUND OF THE INVENTION

1. Introduction

The lenses of human and animal eyes are subject to damage by physical or other external trauma whether accidental or otherwise and by the formation of cataracts. It has been common practice for many years to surgically remove such damaged lenses. An eye with the lens removed is said to be in the aphakic condition. Subsequent to intracapsular or extracapsular lens extraction, the aphakic eye does not have the ability to focus light with the result that the retina receives only a blurred image. Contact lenses, spectacles or a combination of the two have been used in the past with varying degrees of success to focus the light rays to restore vision. The use of contact lenses and eye glasses to overcome aphakia is subject to the fundamental drawback that such devices are located outside of the eye which results in a shift of the focal point from the natural position within the eye. This results in distortion and/or a change in size of the image. Moreover, eyeglasses cannot restore normal binocular vision if the other natural eye remains and contact lenses must be in continuous use to maintain vision in the aphakic eye.

Cataracts are a common disorder of the eye and are the second leading cause of blindness in the United States. A cataract is a physical change in the structure of the lens of the eye which causes transformation of the normal transparent lens to a cloudy or opaque state. The function of the lens is to focus light rays to form a perfect image on the retina. Cataracts interfere with the focusing of the light rays causing the image to become blurred and eventually leading to blindness if unattended. The opacities caused by cataracts are often not distributed uniformly so that the lens has both opaque and clear areas. Therefore, the degree of loss of vision depends on the size, location and density of the opacities.

There are several basic types of cataracts including congenital cataracts; traumatic cataracts caused by accidental injury; and most common of all, senile cataracts, most prevalent in the elderly. It is not known why senile cataracts develop and the process may proceed over a period of months or even years before treatment is required. At present, the only successful treatment is surgical excision and replacement of the cataractous lens.

The lens of the human eye contains a hard central nucleus within a cortex. Disruption of the perfectly aligned fibers of the cortex and nucleous causes opacities. Large areas of the cortex and nucleus thus gradually become opaque until the image on the retina is blurred. At this point, the cataract has progressed to a stage where some of the resolving power of the eye is lost due to the damage to the lens.

A cataract is treated by relatively simple surgery under local anesthesia in which the lens material affecting vision is removed. Approximately one half million Americans undergo such surgery every year, cataract or lens removal being the most frequently performed operative procedure by ophthalmic surgeons in the United States.

During the operation, the surgeon views the operation site through a high powered microscope which greatly magnifies the eye to facilitate the procedure. The eye is kept moist with physiological saline throughout the procedure.

In the past, standard procedure for removing the damaged lens involved first dilating the pupil and then making a half circle incision at the junction of the sclera and the clear cornea. The upper half of the cornea was reflected and the iris was retracted to provide access to the entire lens. The lens was then removed by one of several techniques. For example, the lens may be drawn or eased out through the incision by means of a cup-shaped suction fixation instrument called an erysiphake. The lens may also be removed by a cryoadhesion (freezing) technique known in the art. Such procedures are known as intracapsular techniques, since the entire lens and capsule is removed.

Another method is to excise the anterior capsule, shell out the nucleus, and vacuum out the cortex. This is an extracapular technique.

Regardless of the technique of removing the lens, the incision must be large enough for this purpose and must be sutured to complete the operation. The patient requires from about 48 hours to one week to convalesce from such operations due to the discomfort and irritation caused by the large incision.

In recent years intraocular lenses have been developed for implantation in the eye after the cataractous or otherwise damaged lens has been removed, thereby eliminating the need for contact lenses or eyeglasses after surgery.

The first intraocular lens was implanted in a human eye in 1949. From its inception, the intraocular lens has had a tumultuous history. The controversy has centered around the placement, location, design and surface quality of the artificial lenses.

In Applicant's above-referenced prior application, an expansile artificial intraocular lens was disclosed, that is, a dry lens capable of insertion through an incision of minimal length which lens expands upon implantation to an optically correct lens. By minimizing the incision through which such a lens can be implanted; discomfort, irritation and, therefore, convalescence are reduced. Having generally set forth the requirements for expansile lenses in such prior application, and expansive lens having particularly novel features is hereafter set forth.

2. Field of the Invention

This invention relates to the field of intraocular lenses and more particularly to expansile intraocular lenses. Specifically, the invention relates to an artificial intraocular lens having novel features of construction and arrangement which serve to center the optic portion of the lens on the optic axis.

3. Description of the Related Art

Existing intraocular lenses are made of a clear, hard plastic material or glass, usually plano-convex. Such lenses are ground and polished to predetermined specifications for the range need for human lens replacement. Over the years such lenses have had a broad range of forms and sizes. Basically, such lenses are a disc with or without suspensory projections about its periphery. The projections, in whatever form, suspend the lens within the anterior or posterior chamber. Such projections are commonly called haptic loops. These loops emanate from the periphery of the optic or clear portion of the lens. Such haptic loops may be curved, or be in the form of J's. The thin loops can be made of prolene (polypropylene) and fit into holes in the optic or lens. The loops are then permanently affixed to the lens.

Whatever form the lens takes, it must be oriented along the visual axis within the eye. The visual axis is an imaginary line which passes axially through the center of the lens and extends through the pupil and cornea. The lens must be centrally oriented along this axis in the path of the light to the retina. The curved front and back surfaces of the lens or disc must be positioned on the same axis to provide an optically correct orientation. The purpose of the haptic loops is to anchor the lens in a central position along the visual axis. The curved portion of the loops contact the chamber walls and hold the lens in place.

The original intraocular lenses posed many problems associated with their use. Many such lenses, having loops of nylon or of plastic also showed marked biodegradation of the loops, after prolonged periods of use, where the chamber angle was contacted due to the biological reaction between the loop material and adjoining structures. Many loops were digested completely leaving the lens free floating in the chamber and no longer aligned in the visual axis. Other problems occurred as the result of the surface finish on many of the early implants. Analysis showed sharp grooves in the surfaces formed from lathe polishing. Edge aberrations of the lenses also caused chronic irritation. It was also found that lenses of too large or too small a size caused corneal dystrophy. Examination of these early lens implants paved the way for the current knowledge of design requisites for intraocular lenses. Today, the vast majority of cataract operations performed in the United States involve implanting intraocular lenses.

Cataract surgery incorporating implantation of an intraocular lens is similar to the operation performed without implantation. However, there is no single method followed by all surgeons. Generally, a large incision, approximately 10 mm, is made in the conjunctiva and limbus where the cornea and the sclera meet. The cataractous lens nucleus is then shelled out. The remaining cortex is aspirated to leave a clear lens capsule. A relatively new process called phaco-emulsification allows this incision to be reduced to 3 mm. Phacoemulsification, an extracapsular technique, involves ultrasonic fragmentation of the lens into small particles. Once this has been accomplished, the particles are removed by suction leaving a clean capsule free from cataractous material, and only a small opening in the eye. However, the present relatively large-sized implants require enlarging the incision to at least 7 mm to accommodate the introduction of the intraocular lens. The lens is placed and positioned in the posterior chamber to provide an optically correct visual axis. The loops rest and anchor the lens against the capsule walls. Positioning the lens is a delicate technique with surgeons using different lenses and procedures. However, one procedure which is typical is to anchor or fix the lens in position by suturing one or more of the haptic loops. Alexeev, U.S. Pat. No. 4,316,292 issued Feb. 23, 1982, describes a lens wherein one haptic loop is stitched.

While intraocular lenses are becoming popular in present day ophthamology, many designs are still experimental and it is not known how long the new lenses will last in the human eye. Ophthamologists usually suggest that older patients have the lens implant. Controversy still remains as to the design and placement of the lens. Aphakic patients must still go through this intricate operation to accurately position the lens and must still convalesce for many days until the incision heals.

Furthermore, by virtue of the hard plastic composition and large size of presently available intraocular lenses, they are technically demanding to position properly. The haptic loops emanating from the lenses are also awkward to manipulate and may cause trauma to the eye if they are not carefully inserted.

The initial incision in the cornea still tends to be large, sometimes more than 7 mm, to accommodate the lens and the protruding loops. The lens is slipped through the large incision, loop end first, and positioned in the posterior chamber. An incision of this size requires post operative care and causes irritation and consequent discomfort to the patient.

In view of the foregoing, it is apparent that the need for heavy glasses or contact lenses after cataract surgery has been eliminated. However, serious problems still exist with the lenses themselves and also with the operating procedures. A considerable body of patent art exists in this field of which the following is representative.

Thiele, U.S. Pat. No. 3,553,299 issued Jan. 5, 1971, describes a process for making replacement eye lenses by dissolving the lenses of the eyes of warm blooded animals and processing the resulting material to form a gel from which the replacement lens is formed.

Cordrey et al U.S. Pat. No. 3,943,045 issued Mar. 9, 1976, describes a process for making hydrophilic polymers suitable for use as contact lenses or surgical implants, among other things. Highgate, U.S. Pat. No. 3,961,379 issued June 8, 1976, also discloses hydrophilic polymers such as polymethyl methacrylate and hydroxyethyl methacrylate which are suitable for use in making contact and prosthetic lenses.

Flom, U.S. Pat. No. 3,991,426 issued Nov. 16, 1976 describes artificial intraocular lenses for implantation in the posterior chamber of the eye. This reference also summarizes in considerable detail the history and development of artificial intraocular lenses and the need for them.

Banko, U.S. Pat. No. 4,253,199 issued Mar. 3, 1981 discloses deformable lenses for surgical implantation which are composed of a hydrophilic acrylic polymer, such as "Hydron", which is used for soft contact lenses. The lenses are filled with a suitable liquid or semi-viscous material such as a sterile solution or gelatin, or Ringer's solution, and sealed prior to implantation.

Tennant, U.S. Pat. Nos. 4,254,509 and 4,254,510, each issued Mar. 10, 1981, disclose artificial intraocular lenses composed of rigid materials such as polymethyl methacrylate or soft materials such as hydroxyethylmethacrylate; the rigid material being used for the lens only or for the entire implant and the soft material being used only for the supporting members in other embodiments.

Kelman, U.S. Pat. No. 4,092,743 issued June 6, 1978, describes an artificial Intraocular lens designed in an attempt to minimize incision length. Since the Kelman lens is full size upon implantation, the minimization of incision length is still not complete. Further, it has been found that this lens was too small in the eye, permitting passage of unfocused light rays around the edge of the lens.

The entire disclosures of U.S. Pat. Nos. 3,943,045; 3,961,379; 3,991,426; 4,092,743; 4,253,199; and 4,254,509 are hereby incorporated herein by reference.

It is apparent from the foregoing, that while much work has been done in this art, there still remains a need for an improved intraocular lens and an improved, less traumatic procedure for the implantation of such lenses.

As described herein, and as was disclosed in prior application Ser. No. 520,187, which is incorporated herein by reference, an expansile intraocular lens is used to overcome many of the above problems. Such lens is implanted in a dry or xerogel state through a minimal width incision, such as that used in the extracapsular technique of phaco-emulsification, and becomes hydrated by the fluid present in the eye. The term "dry state" as used herein includes a lens having a wetted outer surface for ease of implantation. However, the bulk of the lens is in the xerogel state. Hydration of the lens results in the expansion or swelling of the lens to an optically correct lens.

To minimize movement of an implanted expansile lens, a patient has to remain still until sufficient expansion has occurred to ensure relative centering of the lens. It is, therefore, desirable to have an expansile lens which becomes centered relatively quickly, preferably immediately, upon implantation.

Koeniger, U.S. Pat. No. 4,449,257 issued May 22, 1984 and filed May 3, 1982, appears to disclose an intraocular lens made from HEMA. No structure or technique is disclosed for immediate centering of the lens upon implantation. Further, since the lens is designed so that only an optic replaces the eye's natural lens, fixation of the lens is said to be obtained by frictional engagement with the capsule. Consequently, due to physical demands of a lens of that size, it cannot be inserted through a minimal width (approximately 3 mm) ocular incision.

It is an object of the invention to provide an intraocular lens which does not require long time periods for centering but which is self-positioning on the optic axis immediately on implantation.

It is still another object of the invention to provide an improved intraocular lens and method for its implantation which reduces the size of the incision required and thus trauma to the eye and consequently reduces convalescent time and discomfort to the patient.

It is a further object of the present invention to provide an intraocular lens which expands after implantation to form a soft lens with soft haptic loops incapable of damaging the capsule interior and which is thus suspended centrally along the visual axis of the eye.

It is a further object of the invention to provide an expansile intraocular lens having haptic loops which center the optic portion of the lens along the visual axis of the eye and which become soft upon implantation in significantly less time than the optic portion.

It is a further object of the invention to provide an expansile intraocular lens preferably having two haptic loops positioned in diametrically opposed locations about a central optic portion, wherein the haptic loops are shaped to conform to and gently engage the capsular sac at diametrically opposed points providing support for the central optic portion.

SUMMARY OF THE INVENTION

The foregoing and other objects of the invention, which will become apparent below, are achieved by providing an improved artificial intraocular lens which is capable of implantation through a much smaller incision than was previously required and having non-traumatic support or positioning means, such a lens is self-supporting and self-aligning on the optical axis upon implantation.

The new artificial intraocular lenses, while composed of materials previously available and used in this art, are designed to make use of a property of these materials in a novel way which was not previously recognized in the art. More specifically, the new lenses are designed and formed to take advantage of the hydration of hydrophilic materials so that they swell and expand in size. This permits the new lenses, prior to implantation, to be much smaller than the natural lens or any previous artificial lens, since they are hydrated by the fluid present in the normal eye so that they expand to the predetermined desired optically correct size. The new lenses are composed of a dry, solid hydrophilic material capable of hydration and have a minimum diameter of about 2 mm and a maximum diameter of only about 5 mm in the dry state, which is less than the diameter of the natural lens. This permits the implantation of the new lenses through an incision corresponding to the 5 mm maximum diameter, at most, and in some cases through an incision of only about 2 mm. This compares to the lenses of the prior art which required an incision of at least 7 mm and up to 12 mm or more.

These new lenses, when hydrated by the fluid present in the eye, expand to a final diameter of from about 6 mm to about 14 mm to provide a predetermined, optically correct lens for the particular patient. Depending upon the particular hydrophilic material employed, the expansion on hydration varies from about 1.5 to about 3, or even up to about 20 times the diameter. Also depending on the particular hydrophilic material employed, the time required for full hydration and expansion of the complete lens varies.

One of the problems associated with expansile intraocular lenses is that while hydration is occurring and the lens is expanding to generally fill an implantation site cavity, movement and possible disorientation of the lens relative to the optic axis can occur. By including haptic loops which are substantially less in cross-sectional dimension than the central portion of the optic or lens and by making the effective length of the haptic loops equal to or slightly larger than the diameter of the implant site, i.e. capsular sac or anterior chamber, hydration of the haptic loops occurs substantially sooner than the central optic portion. Fixation of the lens in a centered position is achieved relatively quickly and expansion occurs substantially uniformly about the optic axis. Therefore, the time required for surgery and surgical trauma is greatly reduced.

In the preferred embodiment, the intraocular lens in its pre-implantation, dry or xerogel form includes a generally spherical optic member having preferably two suspensory tangentially arcuate haptic loops formed integrally with an projecting from the periphery of the optic member at diametrically opposed positions. The haptic loops have varying radii of curvature forming a French curve-like shape. Curved portions of the haptic loops rest against the anterior chamber or the capsule sac after implantation to anchor the lens in position on the optic axis. As the lens is hydrated by the natural fluid in the eye, it expands and the haptic loops bend inwardly in a fashion to assure centering of the lens without tilting, therefore, obviating optical aberration.

The haptic loops in such preferred embodiment are generally curved and have a cross-sectional dimension substantially less than that of the disc-like central or optic portion of the lens. As a result of their lower cross-sectional dimension, the haptic loops hydrate and become soft much faster than the central portion of the lens. Thus, the central or optic portion of the lens is quickly centered relative to the optic axis such that while expansion of the central portion occurs, deviation from the optic axis will not take place.

The recently developed techniques for removing the damaged natural lens by phaco-emulsification or ultrasonic fragmentation are, of course, necessarily used to gain the advantages of the new minimal diameter lenses and incisions.

The procedure for implantation of the new lenses in their hardened dry state is similar to those previously discussed but includes various improvements. The initial incision made in the cornea of about 2-3 mm is considerably smaller than is possible with prior techniques. A small phaco-needle is inserted through the incision to phaco-emulsify the cataractous lens and remove it by suction, leaving the lens capsule intact. The hard, dehydrated intraocular lens is then inserted through the small incision and implanted in the posterior chamber. The lens in its preferred form has a disc-like center portion with two substantially identical integrally formed haptic loops disposed at diametrically opposed positions. The effective length of the lens is equal to or slightly larger than the lens capsule. The haptic loops fit in the lens capsule and hold the intraocular lens in a central position to provide an optically correct visual axis.

During implantation, the intraocular lens is bathed and is initially hydrated by the aqueous humor which fills the anterior chamber of the eyeball. One particular hydrophilic material when fully expanded is approximately 179% its original diameter. For example, if the lens in its dry state is 4 mm, it will swell or expand to 7 mm. Dependent on material selection, the complete lens will swell to its soft fully hydrated form in a matter of hours. However, the haptic loops of the present invention ensure centering of the lens from the time of implantation until full expansion.

The haptic loops of the present invention are formed substantially less in cross-sectional dimension than the central or optic portion of the lens. Hydration of the loops to a state of sufficient softness for satisfactory placement occurs faster than the remainder of the lens, generally within minutes. Thus, allowing the placement of the lens in a position where the central or optic portion of the lens remains generally centered on the optic axis while the lens becomes fully hydrated. The lens, therefore, can expand to a size larger than the incision site to provide an optically correct visual axis without the need for the patient to remain motionless for long periods of time.

A hydrophilic intraocular lens according to the instant invention offers many advantages compared to present day lenses. The small size of the dry lens before and during surgery permits easy maneuverability and handling. The small incision causes less trauma and allows quicker healing.

In its dry state, the effective length of the lens is slightly greater than or equal to the diameter of the lens capsule. The lens is fixed in position by the forces created at diametrically opposed contact areas between the capsule and the haptic loops. The haptic loops are hydrophilic and of substantially smaller cross-sectional dimension than the optic portion of the lens such that they become soft shortly after insertion.

Once the haptic loops become soft, the lens can be more easily maneuvered by the opthamologist to a preferred position, wherein the optic portion is centered relative to the optic axis. As the lens expands to the fully hydrated state, the haptic loops gently conform to the capsular sac providing more support and ensuring a fixed position in the sac and centering on the optic axis. Since support for the lens increases with expansion, the lens need not be fixed by sutures, thus minimizing trauma. Additionally, a bulb-like terminal end may be provided for each haptic loop. Such a terminal end not only protects against further trauma to the eye but also serves as an anchor for the lens upon the collapse of the capsular sac, which occurs some time after completion of the operation. In the preferred embodiment, the loops being integral with the optic portion will not disengage from the lens body leaving a free floating disc in the chamber as with some previous lenses. Additionally, the loops have a variable cross-sectional dimension which is thickest adjacent the optic portion and tapers to a minimum value at a location prior to such terminal ends. Thus, immediate flexibility of a portion of the loops is ensured for centering of the lens with the remainder of the loops becoming flexible as the optic portion expands and deformation of the loops increases.

The soft hydrated lens also has smooth soft edges less likely to cause additional trauma or discomfort than hard lenses.

In the manufacture of these lenses, the xerogel or dry-hardened material is cast into rods which are cut into discs. The discs are then lathe cut leaving enough material for milling loops in the periphery. The lenses are then polished to provide a smooth surface finish.

The lenses may also be formed by injection molding, spin casting, or any other suitable method.

Virtually, any of the many hydrophilic materials known to the art for use in soft contact lenses, intraocular lenses or other surgical implants may be used if they have suitable optical properties, are capable of being formed into the new lenses, and are capable of hydration in the eye to expand as necessary in the present invention. In addition to the polymethyl methacrylate and hydroxyethyl methacrylate, any biocompatible hydratable material could be used.

BRIEF DESCRIPTION OF THE DRAWINGS

These and other objects of the present invention are hereinafter more fully set forth with reference to the accompanying drawings wherein:

FIG. 10 is a diagrammatic top plan view of a partially expanded lens according to the invention; and FIG. 11 is a diagrammatic top plan view of the lens shown in FIG. 10, fully expanded.

DETAILED DESCRIPTION OF THE PREFERRED EMBODIMENT AND METHOD

Figure 1:
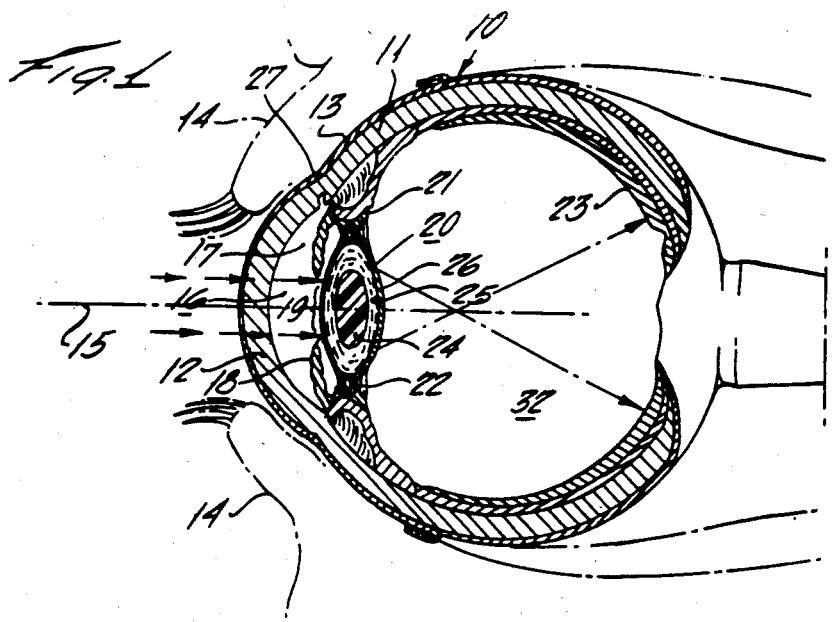
FIG. 1 is a side elevational view, in half section, of a human eye with a normal lens focusing light rays on the retina.

Referring now to the drawings, and particularly to FIG. 1 thereof, the basic parts of the normal human eyeball are illustrated. The eyeball 10 contains a lens 20. The outer coating or white of the eye is called the sclera 11. Along the visual axis 15 there is a clear structure called the cornea 12.

Starting at the edge of the cornea 12 and covering the sclera 11 is a thin, transparent membraneous layer called the conjunctiva 13. The conjunctiva also folds backward to line the eyelids 14 so that the two surfaces glide over one another when the lids blink or the eye moves.

The anterior chamber 16 directly behind the cornea and the front portion of the eyeball, contains an aqueous fluid called the aqueous humor 17.

The iris 18, the colored portion of the eye, is located at the back of the anterior chamber 16. The iris 18 surrounds a central opening called the pupil 19. The muscles of the iris 18 dilate and contract the pupil 19 thereby regulating the amount of light entering the eye.

Behind the iris 18 is the crystalline lens 20 of the eye which in a normal eye is clear, but cloudy if cataractous. A ring-like structure behind the outer edge of the iris 18, called the cilliary body 21, focuses the lens and produces aqueous humor. Zonules 22 stretch from the ciliary body 21 to the lens 20 and hold it in place.

The back portion of the eye contains a large space between the lens 20 and the retina 23. This space contains a jelly-like fluid called the vitreous humor 32.

As seen in FIG. 1, the lens 20 consists of a hard inner nucleus 24 surrounded by the cortex 25. The lens 20 and cortex 25 are encased in a thin elastic elliptically-shaped membrane called the lens capsule 26. The cortex 25 is generally the portion of the lens which becomes cloudy with the onset of cataracts.

One form of cataract can appear as opacity in a spoke-shaped pattern developing at the front and back of the lens capsule 26. The opacity gradually spreads towards the center of the lens 20. Eventually larger and larger areas of the cortex 25 become opaque until the iris casts no shadow. At this stage vision is clouded and a mature cataract is present.

Figure 2:
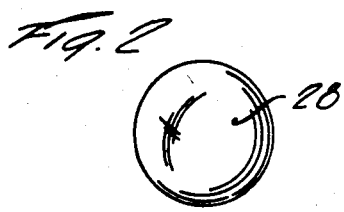
FIG. 2 is a top plan view of an expansile lens without haptic loops prior to implantation.

FIG. 2 illustrates an expansile intraocular lens in its dehydrated form 28. The lens is implanted through a small incision 27A in the limbus 27 and positioned within the open side of the lens capsule 26.

Figure 2A:
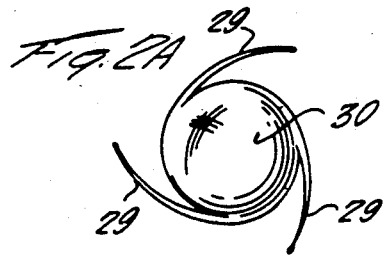
FIG. 2A is a top plan view of an expansile lens with haptic loops carved from the lens disc, also prior to implantation.
Figure 3:
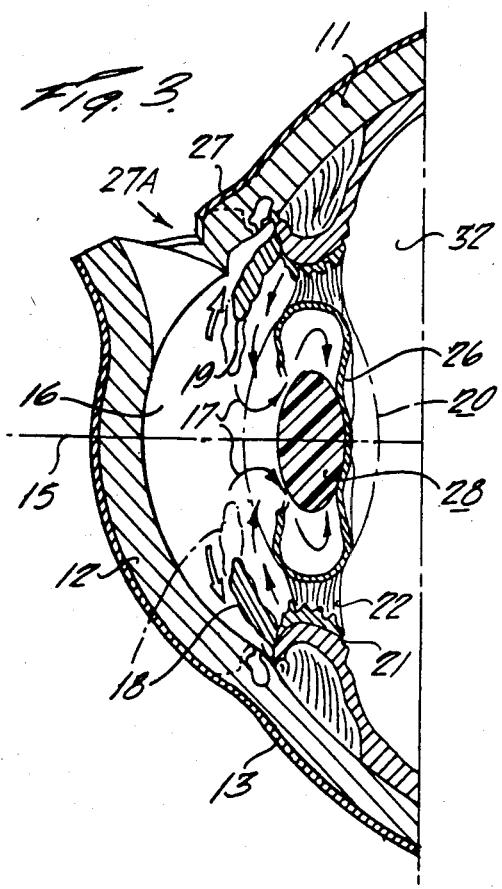
FIG. 3, is a side elevational view, in half section, of a human eye from which the natural lens has been removed showing an expansile lens in its dry state immediately after implantation in the posterior cavity.
Figure 4:
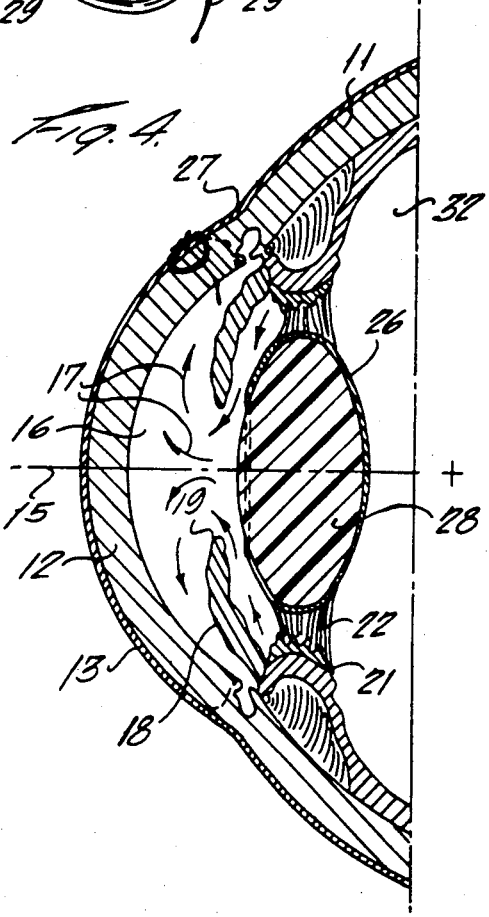
FIG. 4, is a side elevational view of the eye of FIG. 3 after the implanted lens has hydrated and expanded to fill the posterior cavity and align itself on the optic axis.

The dry, hardened plastic disc 28 is composed of a suitable hydrophilic material, which is ground to the predetermined optical power required by the cataract patient. The disc or lens 28 is polished to ensure a smooth surface finish. Enough material may be left on the disc 30 periphery to form tangential haptic loops 29 of the same hydrophilic material, as shown in FIG. 2A.

Figure 5:
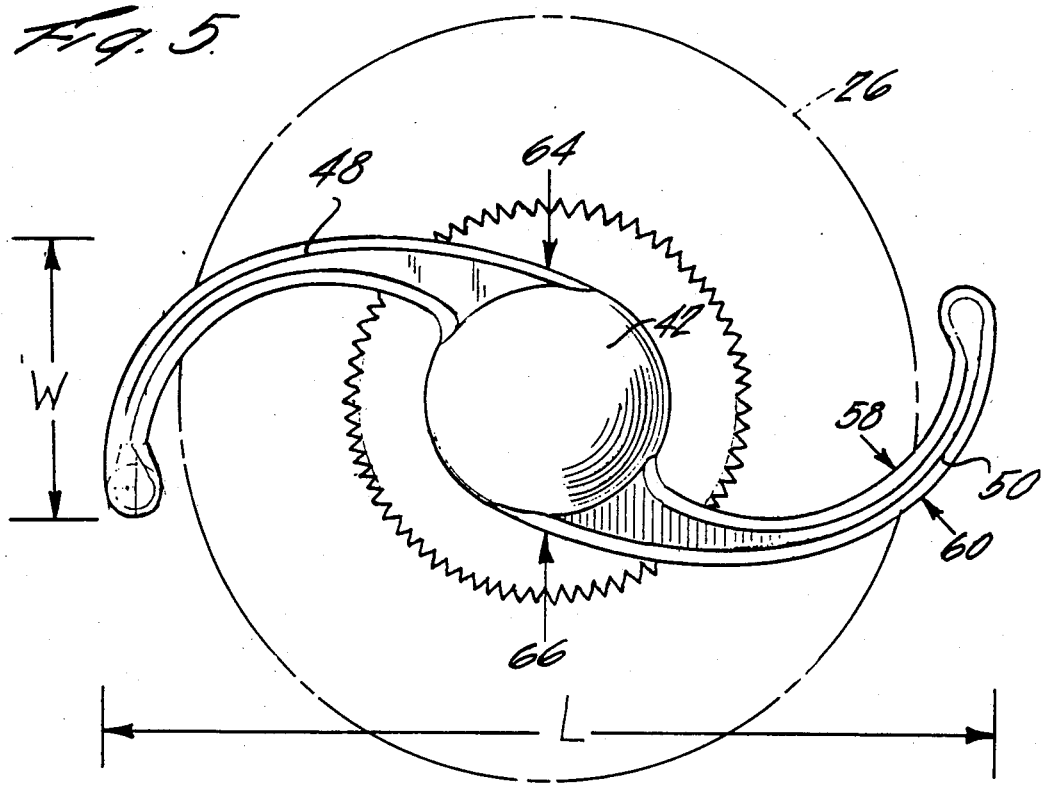
FIG. 5 is a top plan view of a lens according to the invention with haptic loops formed at diametrically opposed locations on the optic portion of the lens with a lens capsule shown in phantom in the background.
Figure 6:
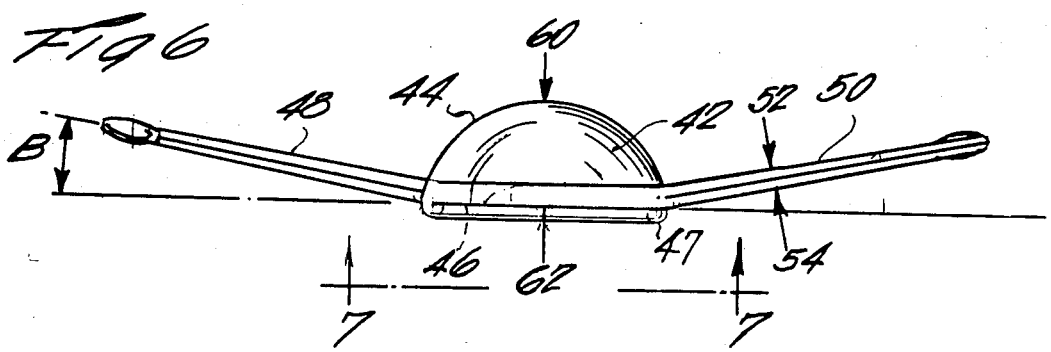
FIG. 6 is a side elevational view of the lens shown in FIG. 5.

FIG. 5 illustrates the preferred form of the instant invention in its dehydrated form. Lens 40 is shown to include a central or optic portion 42 which is generally disc-shaped. Central portion 42 is shown in FIG. 6 to have a convex or dome-shaped surface 44 and a planar or flat surface 46, forming a so-called "piano-convex" lens. Dependent on the dioptic power required to achieve correct visiosn, the planar surface could also be formed in a convex shape. Attached to central portion 42 are haptic loops 48 and 50. In the preferred embodiment, such haptic loops are integrally formed with central portion 42, project radially therefrom and are generally C-shaped.

Haptic loops 48 and 50 are shown in FIG. 5 to be diametrically opposed and uniform with central portion 42. Curving the bulb-like ends 49 and 51 towards central portion 42 ensures that only smooth, relatively gentle rounded surfaces will contact the lens capsule 26 for centering central portion 42 on the optic axis. The effective width W of haptic loops 48 and 50 is shown to be substantially equal to the diameter of central portion 42, namely approximately 3 mm. The lens can thus be inserted through an incision of minimal width. The effective length L of the haptic loops is shown to be slighly larger than the diameter of the capsular sac 26. Since the capsular sacs generally range between 11 to 13 mm, the effective length of the haptic loops will be slightly larger than this range. Although it is recognized that different sized lenses could be provided for different sized capsular sacs. The effective length of the lens together with the diametrically disposed orientation of the loops serves to provide a balance of forces holding the lens in position. Thus once in place, the lens is not likely to move. Non-movement of the lens is further enhanced by the bulb-like terminal ends 49 and 51 of the haptic loops. These ends serve to firmly anchor the lens in position.

Figure 7:
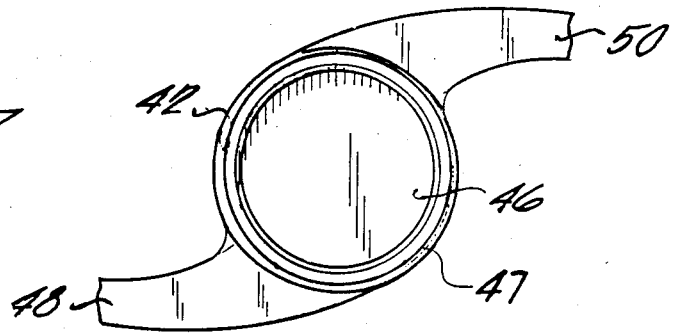
FIG. 7 is a bottom view along the line 7—7 of FIG. 6.

By inclining haptic loops 48 and 50 forward relative to planar surface 46, the planar surface is held against the back wall of capsule 26. The positioning of surface 46 relative to capsule 26 provides the necessary reference for ensuring proper focus of light on retina 23. In the preferred embodiment, the angle of inclination "B" is 10°; however, angle "B" can range from 0° to 15°. It is known that the capsule may opacify following certain implantation surgery. Such a condition is treated by surgically making an opening in the capsule, using either surgical instruments or a laser. In order to prevent damage, i.e. scratches or nicks, to surface 46 during such surgery, a series of button-like projections or a ridge 47 can be formed in a ring pattern on surfaces 46. See FIG. 7. Such structure serves to slightly space the capsule wall from the posterior surface of the lens.

As shown in FIGS. 5 and 6, haptic loops 48 and 50 have cross-sectional dimensions which are substantially less than that of central portion 42. For example, the dimension of haptic loop 48 shown in FIG. 6 between points 52 and 54 preferably is approximately 0.175 mm, and as shown in FIG. 5 between points 56 and 58, preferably is approximately 0.5 mm. As shown in FIGS. 5 and 6, the cross-sectional dimension of haptic loops 48 and 50 increases to maximum values of approximately 0.75 and 0.25 mm, respectively, immediately adjacent optic portion 42. The cross-sectional dimension of central portion 42 at its widest section between points 60 and 62 is approximately 1.25 mm while the diameter of central portion 42 between points 64 and 66 is approximately 3 mm.

The differnce in dimension between hapticl loops 48 and 58 and central portion 42 results in the haptic loops expanding and softening substantially quicker than central portion 42. Softening of the loops in the area of minimal cross-sectional dimension, sufficient to allow proper placement of the lens, occurs almost immediately. Thus, in a short time span, central portion 42 can be fixed in position with reference to optic axis 15 and the surgical incision can be closed. The conclusion of the surgical procedure is, therefore, independent of the hydration of central disc portion 42. Thereafter, the remainder of haptic loops 48 and 50 expand and become soft allowing for the expansion of optic portion 42 and further deformation of the haptic loops, as shown in FIGS. 10 and 11. It will also be understood that as haptic loops 48 and 50 deform due to expansion of optic portion 42 that greater contact will occur between capsule 26 and the haptic loops. Thus, further centering support is provided central portion 42 as it expands in size.

Haptic loops 48 and 50 are also provided with bulb-like terminal portions 53 and 55. Terminal portions 53 and 55 which serve to anchor the lens within capsule 26.

With reference to FIGS. 8 and 9a–e, inclusive, consider now the surgical procedure involved in implantation of the intraocular lens of the present invention. The surgeon is aided by a high-powered microscope, and views the implantation site through magnified eyes. A 3 mm incision 27A, for example, is made in the limbus 27. The phaco-emulsification probe or needle is inserted through the incision and contacts the lens 20 through the pupil 19 which has been dilated. The probe shatters the lens 20 and removes the nucleus 24 and cortex 25 leaving the capsule 26 intact.

The surgeon guides the small hardened intraocular lens 28 through the incision in the limbus. The intraocular lens 28 travels into the posterior chamber 16 through the dilated pupil 19. Once through the pupil 19, one of the haptic loops is fitted against the wall of the lens capsule 26. Since softening of the lead haptic loop is already occurring, the surgeon can now delicately maneuver the opposing loop against the opposite wall of the lens capsule 26. In the preferred embodiment, holes 49 and 51 are provided in haptic loops 48 and 50 to aid the surgeon with this maneuver. The intraocular lens is now suspended within the capsule 26 by the haptic loops 48 and 50 which position it on the optical axis 15. The incision is then sutured.

Figure 9A:
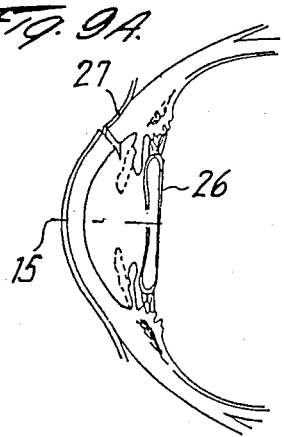
FIGS. 9 A-E are a sequence of views depicting an eye from which the natural lens has been removed, the implantation of a lens according to the invention, a lens positioned in the posterior cavity shortly after implantation, a fully expanded lens in the posterior cavity and a fully expanded lens which has been positioned in the anterior chamber.
Figure 9B:
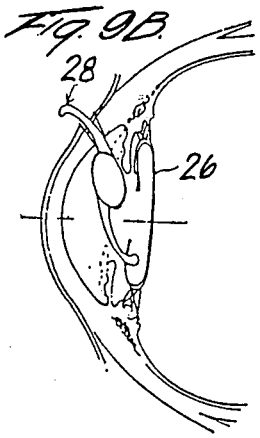
Figure 9C:
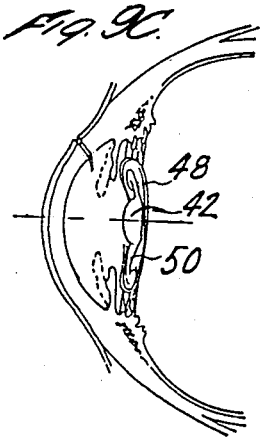
Figure 9D:
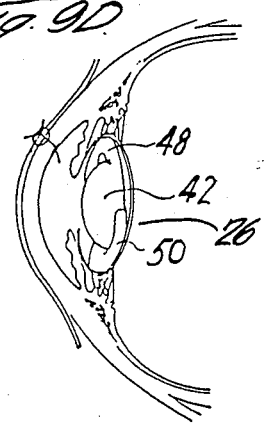
Figure 9E:
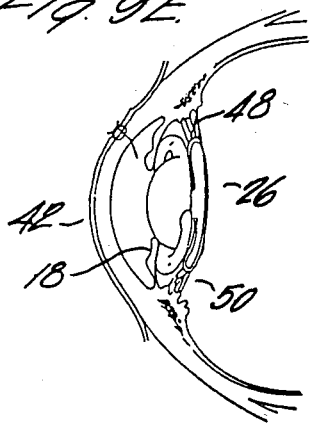

The dry intraocular lens 28 now immersed in the aqueous humor solution 17 of the eye, further expands until it reaches its maximum size shown in FIG. 9d within about 1 to about 24 hours after being implanted so that it substantially fills capsule 26. The expansion of central portion 42 causes the haptic loops to circumferentially contract towards its periphery and push toward the capsule wall. The intraocular lens 30 is now a soft expanded disc of sufficient size to avoid spherical and edge aborrations and is positioned on the optical axis 15. FIG. 9e shows the lens fully expanded having been placed not in lens capsule 26 (capsule fixation) but in front of the lens capsule, behind iris 18 (sulcus fixation).

EXAMPLE 1

Dry, solid hydrophilic rods of "hydron" acrylic polymer, for example, are cut into pellets which are then lathe cut into discs. The patient's corneal curve may, for example, measure 4150 diopters with an axial length of 24 mm. In this case, by calculation using known formulas, the disc would suitably be ground to an optical power of 19.4 diopters. Two haptic loops are formed in a generally French-curve shape integral with the disc periphery emanating from opposite positions. The disc or lens is then tumble polished to provide a smooth surface finish absent any spherical or edge aberrations.

As shown in FIG. 1, the patient's eyelids are spread open using an eyelid speculum 70. The area around the eye is injected with xylocaine to immobilize the muscles. Lidocaine is administered in drops to numb the eyeball. The patient's eye is placed directly below a high powered microscope so that the operation site is magnified.

An incision 72 approximately 3 mm wide is made in the conjunctiva and limbus (where the cornea and sclera meet) exposing passage to the crystalline lens of the eye through the pupil region. The incision and eye are kept moist with a saline solution throughout the operation.

The ultrasonic tip cuts the lens material into small particles that are aspirated through the needle. The remaining lens cortex material is then aspirated leaving the lens capsule intact.

Figure 8:
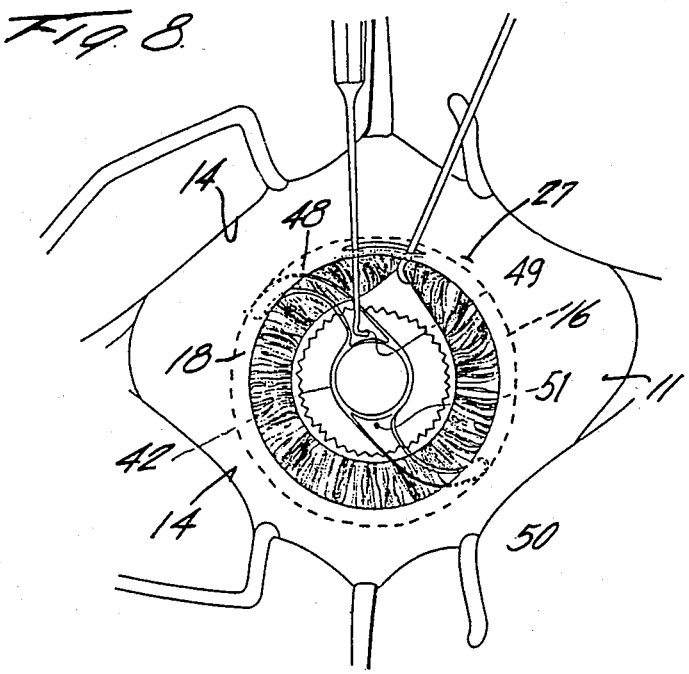
FIG. 8 is a front view of a lens according to the invention being implanted in an eye.

The surgeon manipulates the artificial intraocular lens thorugh the incision into the pupilary area. The lens is then positioned in the center of the capsule with a loop supporting the lens on opposite sides of the capsule wall as shown in FIG. 8. Depending on the hydrophilic material chosen, the softening of the haptic loops sufficient for placement generally occurs within 30 to 60 seconds. The limbal incision is then sutured. Since the lens is centered by the haptic loops, and will remain centered, the patient's movements are not restricted by considerations for lens movement. Full expansion of the haptic loops usually occurs within 15 to 30 minutes after implantation (FIG. 10) with full expansion of the central optic portion taking up to one hour to provide an optically correct visual axis with sufficient size to avoid spherical and edge aberrations. The expanded soft lens will generally fill the capsule bag as shown in FIG. 11 and be centered by the haptic loops in the visual axis. In the preferred embodiment, "Hydron" is the hydrophilic material utilized.

The expanded intraocular lens has a soft surface finish of the required optical power needed for the patient to regain perfect vision. Thus, the patient will be able to see and leave the hospital soon after the operation.

As noted above, while "Hydron" hydrophilic acrylic polymer is preferred as the lens material, a wide variety of other commercially available hydratable polymers may be used, including those now used in soft contact lenses. Commercially available materials previously approved for use in soft contact lenses, and which are also suitable for use in the lenses of this invention, include the following:

| Materials Approved For Use As Soft Contact Lenses | | | |
|---|---|---|---|
| Name | Type | Manufacturer | Trade Name |
| Bufilcon A | hema | Burton Parsons | |
| Cabufocon A | CAB | Danker-Wohlk | Meso-lens |
| Crofilcon A | hema | Corneal Sciences | |
| Dimefilcon A | hema | Calcon Labs | Gelflex |
| Droxafilcon A | hema | Opthalmos | Hydralens |
| Etafilcon A | hema | Frontier c/1 | Hydro-marc |
| Hefilcon A | hema | Automated Optics | PHP |
| Lidofilcon A | vinyl | CLM | Sauflon 70 |
| Lidofilcon B | vinyl | CLM | Sauflon 85 |
| Mafilcon A | hema | N & N/Menicon | |
| Ocufilcon A | hema | Urocon Int | Tresoft/Urosoft |
| Phemfilcon A | hema | Wesley-Jessen | Durasoft/Phemecol |
| Polymacon | hema | Bausch & Lomb | Soflens |
| Porofocon A | CAB | Rynco Scientific | Rx-56 |
| Porofocon B | CAB | Soft Lenses, Inc. | CAB-Curve |
| Tetrafilcon A | hema | UCO Optics | Aquaflex/Aosoft |
| Vifilcon A | hema | Warner Lambert | Softcon |

More specifically, recently developed materials which are hydratable and otherwise suitable for use in the new lenses include, for example, a copolymer of glyceryl methyacrylate and methyl methacrylate (MMA) available from Corneal Sciences, Inc. of Boston, Mass. Soft contact lenses made with this material leave a water content of 41-42% and may be worn continuously.

A series of suitable hydrogels produced by Union Optics Corporation are derived from a hydrophobic monomer, glycidyl methacrylate, which is copolymerized with methyl methacrylate and other monomers to provide a hydratable polymer.

Other suitable hydrogel copolymers include a terpolymer of acrylic acid, N-(1,1-methyl-3-oxobutyl) acrylamide, and methyl methacrylate. A hydrogel copolymer of an acrylomide derivative, N,N-dimethylacrylamide, and methylmethacrylate, or similar alkyl derivatives, is also useful.

Copolymers of hydroxyethyl methacrylate (HEMA) and vinyl acetate, and terpolymers of these materials with acrylamide derivatives are also useful.

Copolymerization of MMA (80-90%) with acrylic acid (10-20%), and diverse cross-linking agents, followed by neutralization of the polymerized acrylic acid with a basic substance, such as ammonium hydroxide and ethylenimide yield hydrogels useful for contact lenses. The depth of penetration of the neutralizing agent into the polymer determines the hydration of the lens.

Finally, a hydrogel contact lens which is not made from the familiar acrylic monomers, and does not contain VP ether, is Optamol which is advertised as an allyloxy polymer derivative and appears to be a copolymer of ally 2-hydroxyethyl ether suitable for use in this invention.

In a preferred embodiment of the invention, commercially available hydrated polymers of the type described above are further purified to remove chemical impurities by soaking them in a saline bath for a suitable period of time and then dehydrating them by freeze drying according to procedures known per se to produce dry, but hydrated polymers from which the new lens may be fashioned. This operation may be performed either before or after shaping of the lens.

Even though particular embodiments of the invention have been illustrated and described herein, it is not intended to limit the invention and changes and modifications may be made therein within the scope of the claims presented. Thus, the lens of the present invention may be of shapes and configurations other than those illustrated; for example, it may be oval or elliptically shaped having a minor axis of small dimension to fit through a small incision and haptic loops formed in conjuction with the major axis. Additionally, the lens may be implanted in the posterior or anterior chamber.

What is claimed is:

1. An artificial intraocular lens for surgical implantation to replace a damaged natural lens in an otherwise functional eye of a patient, comprising: a dome-shaped central disc portion, haptic loops formed on said central portion, for centering said central portion after implantation; said central portion being composed of a dry, solid hydrophilic material capable of hydration by the natural fluid present in the eye to expand after implantation to provide an optically correct lens; said central portion having a cross-sectional dimension substantially less than that of the natural lens wherein said haptic loops are configured such that said central portion is centered upon implantation and remains centered during expansion thereof; thus improving the vision of the patient.

2. The lens of claim 1, wherein said haptic loops are formed in a generally curve shape so that said haptic loops conform more closely to the shape of capsular sac as said central portion expands during hydration.

3. The lens of claim 2, wherein said haptic loops are arcuate, generally of a C-shape.

4. The lens of claim 1, wherein said central portion has at least one convex-shaped surface.

5. The lens of claim 1, wherein said haptic loops are integrally formed with said central portion.

6. The lens of claim 1, wherein said haptic loops are composed of a dry, solid hydrophilic material capable of hydration by the natural fluid present in the eye.

7. The lens of claim 6, wherein said haptic loops become hydrated substantially sooner than said central portion.

8. The lens of claim 1, wherein said haptic loops are composed of the same hydrophilic material as said central portion and wherein said haptic loops have a cross-sectional dimension substantially less than that of said central portion; whereby upon implanation said haptic loops become hydrated substantially sooner than said central portion 9. The lens of claim 1, wherein the cross-sectional dimension of said central portion is approximately 5 times as great as the cross-sectional dimension of said haptic loops.

10. The lens of claim 1, wherein the diameter of said central portion after implantation, hydration and expansion is from about 1.5 to about 20 times the diameter prior to implanation.

11. The lens of claim 1, wherein the hydrophilic material is selected from the group consisting of hydroxyethyl methacrylate and "Hydron" hydrophilic acrylic polymer.

12. The lens of claim 1, wherein the hydrophilic material is hydroxyethyl methacrylate.

13. The lens of claim 1, wherein the hydrophilic material is "Hydron" hydrophilic acrylic polymer.

14. The lens of claim 1, wherein the hydrophilic polymer hydrates after implantation to increase the diameter of the lens from about 1.5 to 20 times its diameter prior to implantation.

15. The lens of claim 1, wherein said central portion also includes a substantially planar surface and wherein said haptic loops are inclined relative to said substantially planar surface.

16. The lens of claim 1, wherein said central portion comprises two convex surfaces.

17. The lens of claim 1, wherein the effective length of said haptic loops in the dry state is slightly greater than or equal to the diameter of the capsular sac.

18. The lens of claim 1, wherein the haptic loops further comprise a bulblike terminal portion which anchors the lens upon interstitial growth of the capsular sac.

19. The lens of claim 1, wherein the haptic loops have a variable cross-sectional dimension which is thickest adjacent the central portion and which dimension tapers to a minimum value at a location prior to the terminal ends of the haptic loops.

* * * * *